(12) United States Patent
Majumdar et al.

(10) Patent No.: US 11,534,410 B2
(45) Date of Patent: Dec. 27, 2022

(54) AMPHOTERICIN LOADED PEGYLATED LIPID NANOPARTICLES AND METHODS OF USE

(71) Applicant: University of Mississippi, University, MS (US)

(72) Inventors: Soumyajit Majumdar, Oxford, MS (US); Akash Patil, Malvern, PA (US); Prit Lakhani, North Brunswick Town, NJ (US)

(73) Assignee: UNIVERSITY OF MISSISSIPPI, University, MS (US)

( * ) Notice: Subject to any disclaimer, the term of this patent is extended or adjusted under 35 U.S.C. 154(b) by 23 days.

(21) Appl. No.: 17/265,644

(22) PCT Filed: Aug. 5, 2019

(86) PCT No.: PCT/US2019/045168
§ 371 (c)(1),
(2) Date: Feb. 3, 2021

(87) PCT Pub. No.: WO2020/028916
PCT Pub. Date: Feb. 6, 2020

(65) Prior Publication Data
US 2021/0330598 A1 Oct. 28, 2021

Related U.S. Application Data

(60) Provisional application No. 62/714,338, filed on Aug. 3, 2018.

(51) Int. Cl.
*A61K 9/51* (2006.01)
*A61K 9/10* (2006.01)
(Continued)

(52) U.S. Cl.
CPC .............. *A61K 9/5123* (2013.01); *A61K 9/10* (2013.01); *A61K 9/5146* (2013.01);
(Continued)

(58) Field of Classification Search
None
See application file for complete search history.

(56) References Cited

U.S. PATENT DOCUMENTS

| 6,071,494 A | * | 6/2000 | Unger | A61K 49/223 424/9.4 |
| 8,647,661 B1 | * | 2/2014 | Sachdeva | A61K 8/35 424/443 |
| 2013/0315987 A1 | * | 11/2013 | Lu | A61K 9/19 514/777 |

FOREIGN PATENT DOCUMENTS

| WO | 2009086470 A3 | 7/2009 | |
| WO | 2016036735 A1 | 3/2016 | |
| WO | WO-2016036735 A1 * | 3/2016 | ........... A61K 31/515 |

OTHER PUBLICATIONS

Jeng et al. (Amphotericin B-entrapping lipid nanoparticles and their in vitro and in vivo characteristics, European Journal of Pharmaceutical Sciences, vol. 37, No. 3-4, Jun. 28, 2009, pp. 313-320). (Year: 2009).*

(Continued)

*Primary Examiner* — Melissa S Mercier
(74) *Attorney, Agent, or Firm* — Thomas | Horstemeyer, L.L.P.

(57) ABSTRACT

Compositions of nanolipid carrier molecules comprising PEG molecules and solid and liquid lipids wherein the PEG has a molecular weight of between about 1000 and 5000 are described. Methods of administering nanolipid carrier molecules are also described. Also described is a method for treating fungal ocular infections by topical ocular administration of nanolipid carrier molecules comprising PEG mol- (Continued)

ecules and solid and liquid lipids wherein the PEG has a molecular weight of between about 1000 and 5000.

20 Claims, 5 Drawing Sheets

(51) Int. Cl.
 *A61K 31/7048* (2006.01)
 *A61K 47/18* (2017.01)
(52) U.S. Cl.
 CPC ........ *A61K 9/5161* (2013.01); *A61K 31/7048* (2013.01); *A61K 47/186* (2013.01)

(56) References Cited

OTHER PUBLICATIONS

Mady et al. (Effect of chitosan coating on the characteristics of DPPC liposomes, Journal of Advanced Research, vol. 1, Issue 3, Jul. 2010, p. 17-191). (Year: 2010).*

Jung, et al., amphotericin b-entrapping lipid nanoparticles and their in vitro and in vivo characteristics, EP Journal of Pharmaceutical Sciences 37, 2009.

* cited by examiner

AMPHOTERICIN LOADED PEGYLATED LIPID NANOPARTICLES AND METHODS OF USE

RELATED APPLICATIONS

This application is a national stage entry pursuant to 35 U.S.C. §371 of International Application No. PCT/US2019/045168, filed on Aug. 5, 2019, which claims priority to, and the benefit of, U.S. Provisional Patent Application No. 62/714,338 filed on Aug. 3, 2018, both of which are hereby incorporated by reference in their entireties.

GOVERNMENT INTEREST

This invention was made with government support under Grant Nos. NIH R0IEY022120-01A1 and P20GM104932. The government has certain rights in the invention.

TECHNICAL FIELD

The presently-disclosed subject matter generally relates to PEGylated lipid nanoparticles and methods of use. In particular, certain embodiments of the presently-disclosed subject matter relate to amphotericin B loaded PEGylated lipid nanoparticles (PEG-NLC-AmB) (as lyophilized particles or as a colloidal aqueous dispersion) and the administration to a subject in need thereof. In some embodiments, the polyethylene glycol (PEG) has a particular molecular weight, as described herein

BACKGROUND

Ocular fungal infections if not treated can lead to permanently impaired vision and can be sight/life-threatening in certain cases, such as in immunocompromised patients[1]. Infected superficial ocular tissues, such as the cornea (Keratomycosis), can be treated with natamycin—a polyene antibiotic. Currently, natamycin is the only approved ophthalmic formulation that is available commercially. Natamycin, however, is not very effective against *Candida* which is the most common ocular fungal infection. Once treatment failure with natamycin is observed, physicians switch to other off-label topical antifungals or systemic therapy. However, treatment of infections caused by deep-rooted fungi require potent antifungals, such as amphotericin B, fluconazole, and voriconazole, either alone or in combination (administered topically or systemically). Amphotericin B is a potent polyene anti-mycotic and drug of choice to treat infections caused by invasive pathogenic fungi, such as *Candida* spp., *Aspergillus fumigatus, Cryptococcus neoformans*, and protozoan parasite *Leishmania* spp.[2]. The newer generation azole antifungals, such as fluconazole, voriconazole, and posaconazole, have similar potency and better ocular permeation in comparison to amphotericin B, but retain major disadvantages of the azole class of antifungals: resistance and cross-resistance[2-4].

Despite the potency and clinical utility of amphotericin B, there are various challenges associated with the delivery of amphotericin B. It is practically insoluble in water, methanol, and ethanol; with a molecular weight of 924.1 Daltons; and log P of 0.8, making formulation of an effective ophthalmic dosage form very challenging. Additionally, solution stability and ocular tissue permeation of amphotericin B also manifests as a formidable challenge. Amphotericin B has very poor ocular permeability and an extremely slow flux across cornea as observed in a human clinical study[5]. In general, the complex ocular barriers—such as tear turnover, the complex ultrastructure of the cornea, various metabolizing enzymes, and efflux transporters—reduce ocular bioavailability of topically administered compounds to less than 5%[6-12]

An ocular formulation for amphotericin B is currently not available. Thus, in cases of severe fungal infection, the intravenous preparations (freeze-dried powders) are reconstituted in water for injection, balanced salt solution (BSS) or dextrose 5% solution (D5W) and either instilled topically or as an intravitreal injection, depending on the site of infection. A limitation of the intravenous preparations that are used off-label is that they need to be used within a day following reconstitution with sterile water for injection (as per the instruction from the manufacturer). Furthermore, these formulations do not allow the addition of any preservatives, as it leads to precipitation, which further limits their ophthalmic use since multidose ophthalmic formulations needs to pass the preservative efficacy test requirements.

In recent years nanoparticulate dosage forms have emerged as a promising ocular formulation platform for poorly water-soluble compounds due to enhanced retention on the ocular surface as well as better penetration into the ocular tissues.

A few attempts have been made to fabricate formulations that might enhance the ocular permeability of amphotericin B, e.g. Eudragit® (methacrylic acid copolymer) nanoparticles, chitosan and lecithin-based nanoparticles[13], microemulsions[14], and cyclodextrin-poloxamer nanoparticles[15]. These reports describe amphotericin B nanoparticles or nanodispersion and demonstrate its in vitro anti-fungal activity, drug release profile, ocular irritation studies, and pre-corneal residence kinetics, but lack evaluation of stability, safety, and biodistribution in animal models to show suitability for ocular drug delivery. Furthermore, sterilization of the above formulations and residual organic solvents needs to be assessed to evaluate suitability for ocular drug delivery.

Although a number of polymeric particulate systems have been investigated, use of lipid nanoparticles have risen to the forefront in recent years because of better biocompatibility of lipids with the ocular tissues.

A lipid nanoparticle is a nanoparticle system comprising the drug, or combination of active ingredients/drugs, dissolved or dispersed in a lipid system. The lipid nanoparticles are prepared by mixing a lipid phase and an aqueous phase, under mixing and controlled temperature conditions. The mixture is then passed through a high-shear homogenizer followed by high-pressure homogenization. The resultant mixture (hot emulsion) on cooling to room temperature yields the lipid nanoparticles suspended in an aqueous phase. The lipid nanoparticles exist in the solid state at room temperature forming an opaque to translucent colloidal dispersion in an aqueous medium (also may be referred to as a colloidal aqueous dispersion). The solution can be lyophilized to yield the lipid nanoparticles as a powder or cake. Other known technologies can also be used to prepare the lipid nanoparticles.

A solid lipid nanoparticle (SLN) is a lipid nanoparticle wherein the active, or combination of actives, are dispersed or dissolved in a lipid that exists in the solid state at room temperature. A combination of such lipids may also be used to prepare the appropriate formulation.

A nanostructure lipid carrier (NLC), an advanced version of the SLNs, is a nanoparticle wherein the active, or combination of actives, are dispersed or dissolved in a combination of lipids; at least one of the lipids exists in the solid state at room temperature and at least one of the lipids exists in the liquid state at room temperature. The presence of liquid lipid within the solid lipid matrix allows increased drug loading and also improves formulation stability.

When two or more active ingredients are present in the formulation at least one of the actives is dissolved/dispersed in the lipid phase. The other active/s may be added to the lipid phase or to the aqueous phase. Addition of the active to the aqueous phase can take place before or after the formation of the lipid nanoparticles. When added to the aqueous phase, the active ingredient may either be absorbed/adsorbed on the surface of the SLNs/NLCs or remain dissolved/suspended in the aqueous phase.

In one embodiment all active ingredients are dissolved or dispersed in the lipid phase.

PEGylation is defined as the modification of the surface of the lipid nanoparticles using polyethylene glycol (PEG) of various molecular weights or their derivatives (functionalized PEGs). The PEG may be added as a lipid-PEG conjugate in the lipid phase of the SLN or NLC. The PEG or its derivatives may also be added to the aqueous phase after formation of the SLNs/NLCs following which the added PEG or PEG derivatives adsorbs on to the surface of the SLNs or NLCs.

Mucoadhesive, stable, and/or stealth nanoparticles are achieved by surface modifying agents such as PEG, chitosan, lipids with amine functional group, etc. PEGylation of nanoparticles renders the surface of the nanoparticles hydrophilic and enhances ocular bioavailability through modified interactions with the mucous layer and corneal epithelium[16]. PEGylation also imparts stability to the lipid nanoparticles during processing and storage of the formulation, as well as when the lipid nanoparticles are exposed to biological fluids, such as aqueous humor and vitreous humor. Physical and chemical stabilization is believed to be achieved by reducing steric hindrance between the lipid nanoparticles and reducing contact between the lipid nanoparticles and surrounding substances (e.g. enzymes, oxidants, and other degradation causing agents)[16-19]. PEGylation of lipid nanoparticles can either be attained by conjugation or electrostatic interaction with a lipid on the surface of the lipid nanoparticles. The major advantage of conjugated PEGylation over electrostatic PEGylation is preventing dissociation of the PEG in the aqueous environment[16].

It is important in the present invention for the molecular weight of PEG to be in the range of 1K-5K for drug loading, stability, autoclavability, permeability and antimicrobial activity.

Ophthalmic amphotericin B formulations are currently not available commercially and the intravenous formulations in the market cannot be stored post-reconstitution for more than 24 hours. An ophthalmic amphotericin B formulation would thus provide significant advantages. Of particular interest would be to provide a formulation with good stability that can be administered at an effective dose in ophthalmic formulation. The PEGylated NLC formulations described herein meet these objectives.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are used, and the accompanying drawings of which:

Figure 1:
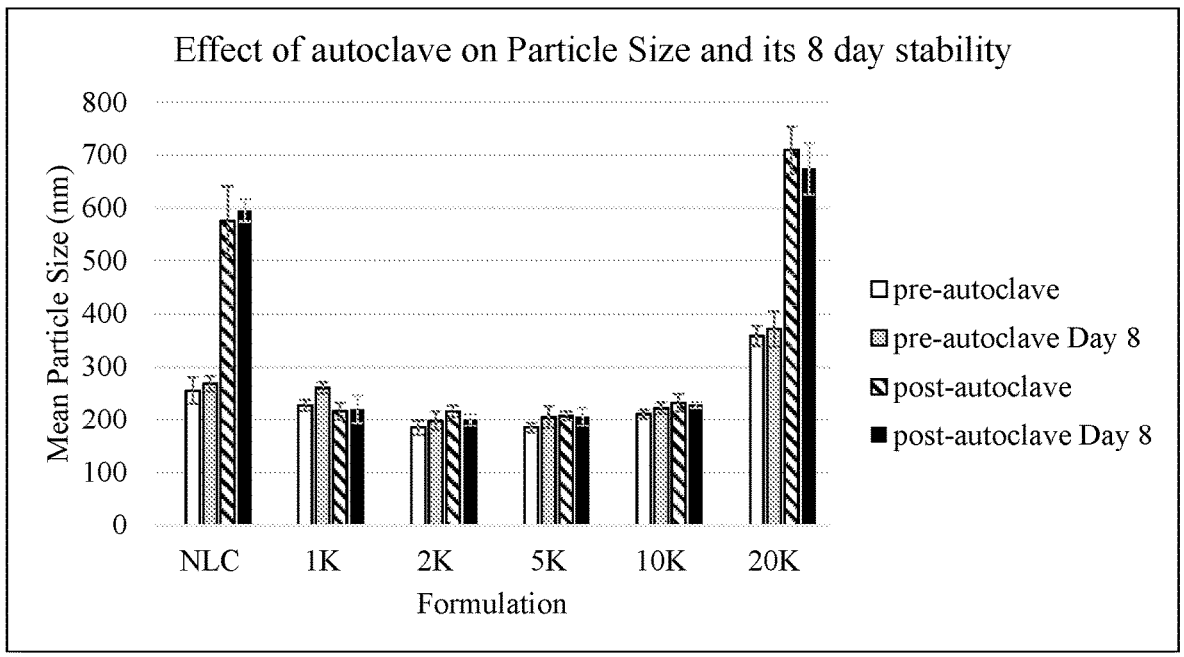
FIG. 1: Evaluation of mean particle size for amphotericin B loaded NLC (PEGylated and Un-PEGylated). mPEG-DSPE was used with varying PEG molecular weight-1K, 2K, 5K, 10K, 20K and their 8-day stability.
Figure 2:
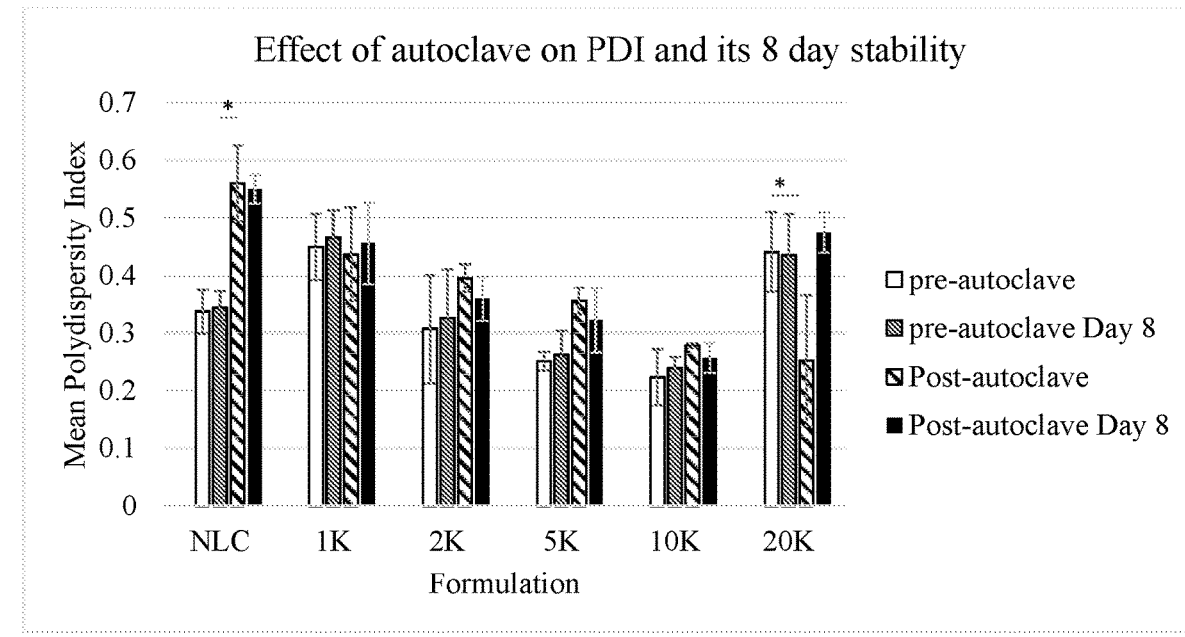
FIG. 2: Evaluation of mean polydispersity index for amphotericin B loaded NLC (PEGylated and Un-PEGylated). mPEG-DSPE was used with varying PEG molecular weight-1K, 2K, 5K, 10K, 20K and their 8-day stability.
Figure 3:
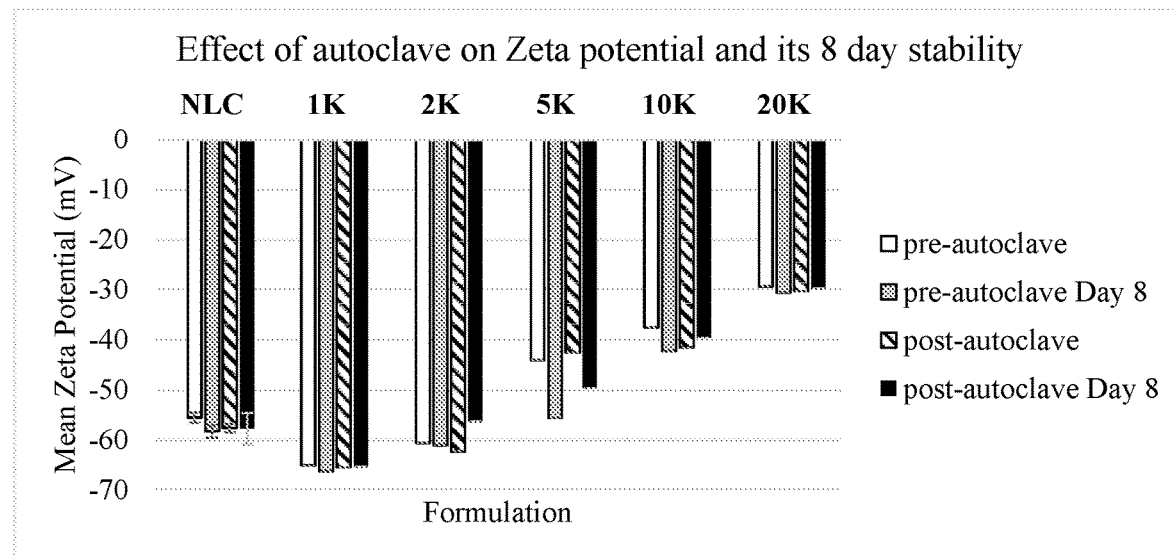
FIG. 3: Evaluation of mean zeta potential for amphotericin B loaded NLC (PEGylated and Un-PEGylated). mPEG-DSPE was used with varying PEG molecular weight-1K, 2K, 5K, 10K, 20K and their 8-day stability. *-Statistical significance $p<0.05$.
Figure 4:
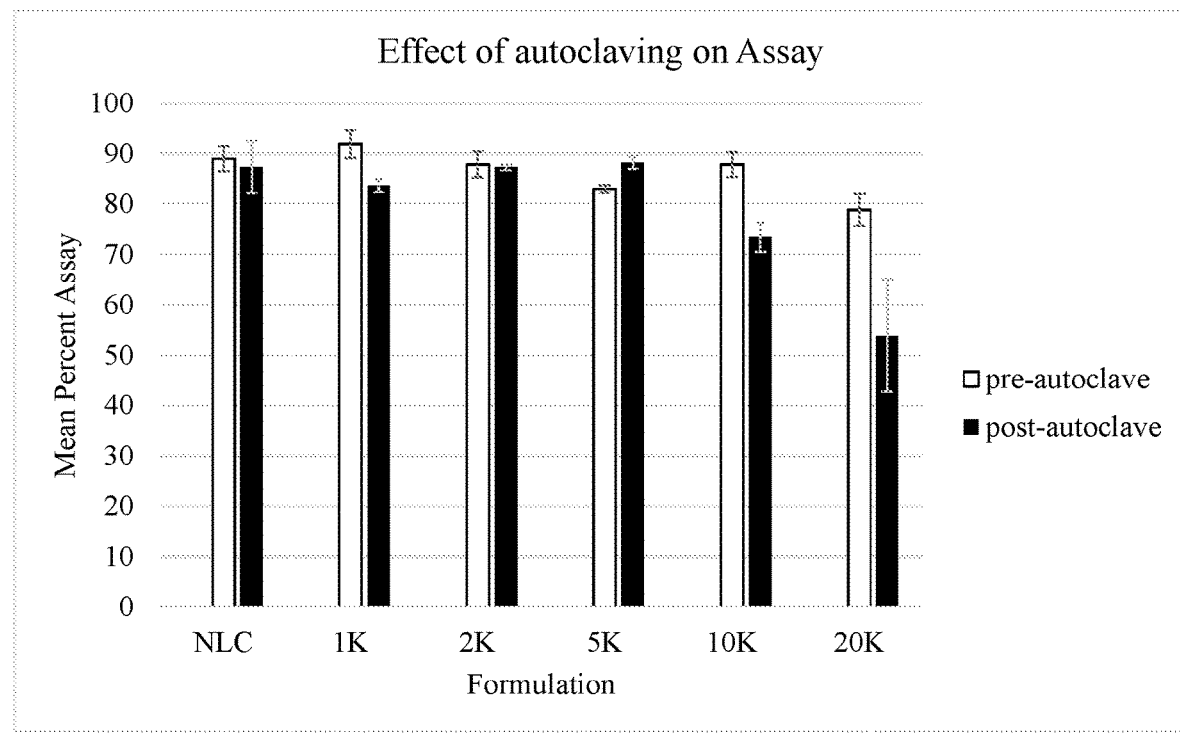
FIG. 4: Evaluation of mean percent assay for amphotericin B loaded NLC (PEGylated and Un-PEGylated). mPEG-DSPE was used with varying PEG molecular weight-1K, 2K, 5K, 10K, 20K. *-Statistical significance $p<0.05$.

The presently disclosed formulations allow enhanced amphotericin B loading in the NLCs prepared using an organic solvent-free process, and a high-pressure homogenizer, to facilitate scale up of the manufacturing process.

DESCRIPTION OF EXEMPLARY EMBODIMENTS

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

While the terms used herein are believed to be well understood by those of ordinary skill in the art, certain definitions are set forth to facilitate explanation of the presently—disclosed subject matter.

To distinguish between the formulations prepared with different PEG molecular weights the formulations have been labeled as the PEG (Mol. Wt of the PEG)-NLC-AmB. Thus, PEG(2K)-NLC-AmB means amphotericin B loaded NLCs that have been PEGylated with a PEG of molecular weight of 2000, whereas, PEG(5K)-NLC-AmB means amphotericin B loaded NLCs that have been PEGylated with a PEG of molecular weight of 5000.

Unless defined otherwise, all technical and scientific terms used herein have the same meaning as is commonly understood by one of skill in the art to which the invention(s) belong.

All patents, patent applications, published applications and publications, databases, websites and other published materials referred to throughout the entire disclosure herein, unless noted otherwise, are incorporated by reference in their entirety.

Although any methods, devices, and materials similar or equivalent to those described herein can be used in the practice or testing of the presently-disclosed subject matter, representative methods, devices, and materials are described herein.

Disclosed herein is the investigation of stabilizing amphotericin B-loaded nanostructured lipid carriers (NLCs) (or any modification of the NLCs that are known to a person skilled in the art) using PEGylation and optimizing it for ocular drug delivery. NLC described here, is defined as a particle in the nano-range that carry drug dissolved/dispersed in the matrix, and/or on the surface, comprising of (not limited to) a lipid or a modified lipid that has melting point above room temperature—either alone or in combination with another lipid or modified lipid that has melting point above room temperature, a surface modifying moiety, biocompatible esterified lipids, and other ingredients.

In some embodiments, amphotericin is loaded at about 1% to about 10% w/w of solid content. In some embodiments, amphotericin is loaded at about 2% to about 7% w/w of solid content. In some embodiments, the amphotericin is loaded at about 4% to about 6% w/w of solid content.

As used herein a particle in the nano-range refers to, in some embodiments, an average particle size of about 100 to about 900 nm; or in some embodiments an average particle size of about 100, about 200, about 300, about 400, about 500, about 600, about 700, about 800, or about 900 nm.

A biocompatible esterified lipid comprises one or more neutral phospholipids selected from the group consisting of 1,2-dilauroyl-sn-glycero-3-phosphate (DLPA), 1,2-dilauroyl-sn-glycero-3-phosphoethanolamine (DLPE), 1,2-dimyristoyl-sn-glycero-3-phosphate (DMPA), 1,2-dimyristoyl-sn-glycero-3-phosphocholine (DMPC), 1,2-dimyristoyl-sn-glycero-3-phosphoethanolamine (DMPE), 1,2-dimyristoyl-sn-glycero-3-phosphoglycerol (DMPG), 1,2-dimyristoyl-sn-1Oolydisp-3-phosphoserine (DMPS), 1,2-dipalmitoyl-sn-glycero-3-phosphate (DPP A), 1,2-dipalmitoyl-sn-glycero-3-phosphocholine (DPPC), 1,2-dipalmitoyl-sn-glycero-3-phosphoethanolamine (DPPE), 1,2-dipalmitoyl-sn-glycero-3-phosphoglycerol (DPPG), 1,2-dipalmitoyl-sn-glycero-3-phosphoserine (DPPS), 1,2-distearoyl-sn-glycero-3-phosphate (DSP A), 1,2-distearoyl-sn-glycero-3-phosphocholine (DSPC), 1,2-distearoyl-sn-glycero-3-phosphoethanolamine (DSPE), 1,2-distearoyl-sn-glycero-3-phosphoglycerol (DSPG), 1,2-distearoyl-sn-glycero-3-phosphoserine (DSPS) and hydrogenated soy phosphatidylcholine (HSPC)—either its true form or further chemically modified, such as DSPE-PEG-2000. Lipids include biodegradable; natural, semisynthetic or synthetic produced; including trilaurate (dynasan112), glyceryl trioleate, glyceryl monopalmitate, glyceryl dipalmitate, glyceryl tripalmitate (dynasan116), tristearate glyceryl trimyristate (Dynasan 114), glyceryl monostearate (IMWITOR 900), glyceryl distearate, glyceryl tristearate, behenic acid mono-, di-, triglycerides and mixtures thereof (glyceryl behenate), stearic acid, palmitic acid, decanoic acid, behenic acid, cholesterol, cetyl palmitate, cetyl palmitate, microcrystalline wax and any other lipid biocompatible for ocular drug delivery. One or more composition of the liquid phase lipid material can be any oil biocompatible for ocular drug delivery, such as, for example, soya bean oil, safflower oil, olive oil, corn oil, sea buckthorn oil, linseed oil, peanut oil, tea oil, sunflower oil, C8~C18 medium chain length triglyceride fatty, fish oil, barley oil, evening primrose oil, vitamin E succinate, vitamin E acetate, caprylic/capric glycerides, miglitol (Miglyo1812), oleic acid or, oleate, ethyl linoleate, isopropyl laurate, isopropyl myristate, ethyl butyrate, ethyl lactate, and the like. One or more of the natural surfactants include soy lecithin, egg yolk lecithin natural, natural or semi-synthetic phosphatidyl choline phosphatidyl choline and derivatives thereof, vitamin E polyethylene glycol 1000 succinate (TPGS), polyethylene glycol hydroxystearate 660-12-(HS-15), polyoxytheylene-8 caprylic/capric glycerides (Lab solid 1), polyvinyl alcohol—distearyl phosphatidylethanolamine (PEG-DSPE), ethylene glycol monoethyl ether (Transcutol), using diethyl succinate acyl sulfonate, poloxamer 188, 182, 407, 908, polyoxyethylene fatty acid esters, polyoxyethylene fatty alcohol ethers, cholic acid, or deoxycholic acid and its sodium salt, glycocholate, one or more of sodium, sodium taurocholate, sodium deoxy taurocholate, butanol, butyric acid, glycerol monooleate and any other surfactant biocompatible for ocular drug delivery.

As disclosed herein, in some embodiments, PEGylated NLCs with PEG molecular weight ranging from 1K-5K results in better drug loading, and physical and chemical stability of amphotericin B, compared to PEGs of other chain lengths. In particular PEGylated DSPE (1,2-Distearoylglycero-3-phophoethanolamine) of particular PEG chain lengths (MW 1K-5K) can improve the loading, stability and autoclavability of the amphotericin loaded NLCs. The transcomeal permeability and in vivo distribution of a PEGylated NLC formulation, representative of the current invention, was similar to that of a commercially available injectable amphotericin B liposome, marketed as Ambisome®. Based on these studies, the NLCs are contemplated for use as a novel treatment that could be used for ocular drug delivery, particularly in topical and intravitreal administration. The presently disclosed amphotericin loaded NLCs are particularly useful for ophthalmic application and are autoclavable and stable at 4° C. for at least 7 days post reconstitution. In some embodiments the formulations include drugs for treatment of ocular infections, including *candida* infections, and demonstrate surprisingly enhanced activity against *Candida albicans* but not against *Aspergillus niger*.

The presently-disclosed subject matter includes NLCs that are functionalized with PEGs of MW ranging from about 1K-10K. In some embodiments, the PEG has a MW ranging from about 1K-5K. In some embodiments, the PEG has a MW of about 1000, 1500, 2000, 2500, 3000, 3500, 4000, 4500, 5000, or 5500. In some embodiments, the NLC comprises castor oil as the preferred liquid lipid. In some embodiments, the NLC is PEG functionalized, and these NLCs are known in the art as PEGylated NLCs. The PEG can be located on the surface of the NLC, and such PEGylation can aid in stability of the NLC. PEGylation can, in some instances, render the surface of the NLCs hydrophilic, enhance ocular bioavailability by modified interactions with the mucous and epithelium of the cornea, and impart improved stability. In some embodiments, PEG can be included in the NLC core without affecting the surface of the NLC and still aid in enhanced drug loading of NLC. In some embodiments, the PEG chain has an average molecular weight of between about 1000 and 10000. In some embodiments, the PEG chain has an average molecular weight of about 2000. The PEG functionalization can be achieved in a variety of ways, and the PEG density and molecular weight can be varied according to the desirable end use of the NLC, including drug loaded, site of application, desired drug loading, and other variables. In some embodiments, the PEG conjugates used for functionalizing the NLCs is 1,2-Distearoyl-phosphatidylethanolamine-methyl-polyethyleneglycol conjugate-2000, mPEG-2000-DSPE.

In some embodiments, the NLC composition can include surfactants and solvents. In some embodiments, the NLC composition can include Tween, 80, Poloxamer 188, glycerin and/or water.

In some embodiments, the subject has or is susceptible to a fungal infection. In some embodiments, the fungal infection is a *Candida* infection. In some embodiments, the infection is fungal keratitis.

In some embodiments the PEG(2K)-NLC-AmB colloidal dispersion (alternatively referred to as colloidal aqueous dispersion) is autoclaved to prepare a sterile dosage form In some embodiments the autoclaved PEG(2K)-NLC-AmB colloidal dispersion is lyophilized, with or without the addition of suitable cryoprotectants to get a sterile, lyophilized powder which can be used for parenteral or ophthalmic (topical, periocular or intravitreal) administration in suitable dosage forms.

Alternatively, the colloidal dispersion can be first lyophilized and the dried nanoparticles can then be autoclaved to get a sterile, lyophilized powder which can be used for parenteral or ophthalmic (topical, periocular or intravitreal) administration in suitable dosage forms.

In some embodiments the unsterilized PEG(2K)-NLC-AmB colloidal dispersion may be lyophilized to obtain nonsterile, lyophilized powder that can be used for oral (buccal, oral cavity or gastro-intestinal application) administration as a mouthwash (reconstituted), embedded in ointments, gels, in situ gelling systems, creams, films, capsules, tablets, dry powder, solid dispersion, nasal spray or irrigation system or any other dosage form known in the art.

Some embodiments provide for a method of administrating the NLC as disclosed herein to a subject. In some embodiments, an effective amount of the NLC is administered to a subject in need thereof. In some embodiments, the effective amount is about 0.05% w/v to 0.5% w/v. In some embodiments, the effective amount is about 0.05% w/v to 0.3% w/v.

In some embodiments one or more other antifungal agents may be combined with Amphotericin B to potentiate the antifungal activity of amphotericin B. These compounds may be incorporated in the lipid phase along with amphotericin B or may be present aqueous phase of the colloidal dispersion or as a surface coating on the PEG(2K)-NLC-AmB, or both.

In some embodiments one or more other pharmaceuticals such as antibacterial, chemotherapeutic, anti-inflammatory, enzyme/transporter inhibitors etc. may be combined with Amphotericin B. These compounds may be incorporated in the lipid phase along with Amphotericin B in the PEG(2K)-NLC-AmB or may be present in the aqueous phase of the colloidal dispersion or as a surface coating on the PEG(2K)-NLC-AmB, or both.

In some embodiments, additional agents are included in the aqueous phase as stabilizers, surfactants, surface modifiers, viscosity, or permeation enhancers. Non-limiting examples of such agents include chitosan, peptides, cyclodextrins, lipids, and sphingolipids.

In some embodiments a preservative may be added to the formulation at the time of reconstitution.

Methods of making the NLCs are also disclosed herein. According to one or more of the embodiments disclosed herein, certain methods of manufacturing the NLCs permits higher drug loading than the previous reports—more than 10-folds higher concentrations can be achieved in the colloidal dispersion state. In some embodiments, the PEGylated NLCs are made by the step of emulsifying a lipid phase and aqueous phase at high temperature (above the melting point of the solid lipids) to produce an emulsion and the step of homogenizing the hot emulsion, which can include a step of applying one or more cycles of high-pressure homogenization (HPH).

On cooling the hot emulsion, SLN or NLC dispersion is formed as the nanoparticles come out of the aqueous phase forming a dispersion of colloidal particles in the aqueous phase. Accordingly, the final product, upon cooling, can be a colloidal dispersion of solidified lipid nanoparticles (SLN or NLC) in an aqueous phase. During processing at higher temperatures the dispersion could be a lipid droplet dispersion, but on cooling to room temperature the result is a solid lipid phase or a liquid lipid phase in a solid state lipid.

It is noted that the formulation can be lyophilized to get a powder state for reconstitution or filling in capsules and or other dry powder formulations.

In some embodiments, the concentration of amphotericin B in the colloidal dispersion following one or more states of reconstitution is about 0.05% w/v to 0.5% w/v. In some embodiments, the concentration is about 0.05% w/v to 0.3% w/v.

In some embodiments, the step of emulsifying comprises hot-melt emulsification. In one embodiment, emulsifying includes heating a lipid phase, optionally containing amphotericin B, to about 75° C., adding an aqueous phase to produce an emulsion.

In some embodiments, the step of homogenization includes homogenization of the coarse hot emulsion to produce a fine hot emulsion. A step of HPH can be included subsequent to the production of the emulsion and includes a cycle of applying about 500 to 1500 bars of pressure for about 5 to about 30 minutes. In some embodiments, about 20 to about 50 cycles of HPH are preferably used in preparing the NLCs. In some embodiments, about 30 cycles of HPH are used.

In some embodiments, the lipid phase in the PEGylated NLC colloidal dispersion comprises of 0.5-2.0% w/v mPEG-2000-DSPE, 0.01-3% w/v amphotericin B and 1-3% w/v castor oil. In some embodiments, the lipid phase can include additional components, including glyceryl palmitostearate.

In some embodiments, the PEGylated NLCs have an amphotericin B loading of about 4.6% w/w (expressed as a % of the lipid content). The nanolipid carriers produced are preferably an average particle size of between about 100 nm to about 900 nm, preferably about 200 to about 700 nm and more preferably 200-400 nm. In some embodiments, the nanolipid carriers have a polydispersity index (PDI) of about 0.3.

In some embodiments, the methods of making the formulation produces an amphotericin B loaded PEGylated NLC with about 90% or more entrapment efficiency.

The amphotericin B loaded PEGylated NLCs disclosed herein can be optimized to provide a formulation, with at least 15-day stability at 4° C., in the colloidal dispersion state. Advantageously, these colloidal dispersions are autoclavable.

Additionally, or alternatively, in some embodiments, a kit may be provided for use in the methods disclosed herein. In some embodiments, the kit includes the amphotericin B PEGylated NLCs, and optionally a device for applying the formulation to the eye, for example an eye dropper.

The presently-disclosed subject matter is further illustrated by the following specific but non-limiting examples. The following examples may include compilations of data that are representative of data gathered at various times during the course of development and experimentation related to the present invention.

EXAMPLES

Example 1: Lipid Screening—Castor Oil and Precirol™

Lipid screening is a crucial step, in order to select the lipids with the highest drug solubility and/or dispersibility. Amphotericin B (1 mg) was added to the lipid at 75° C., upon stirring at 2000 rpm for 10 mins, and observed with naked eye as well as under the microscope for precipitation/aggregation. Amphotericin B has a relatively higher solubility at elevated temperature in Precirol™ ATO 5 (glyceryl palmitostearate) in comparison with the other lipids, such as Compritol® ATO 888 (glyceryl behenate), stearic acid, glyceryl mono stearate (GMS) and glyceryl di-stearate (Table 1). However, it showed a small amount of drug aggregated at the bottom of the vial. While screening liquid lipids, amphotericin B better dispersed/solubilized in castor oil (Table 1).

TABLE 1

Lipid Screening test.

| Liquid Lipid | Solubility/Dispersion | Solid Lipid | Solubility/Dispersion$^c$ |
|---|---|---|---|
| Labrafilm | | Compritol | − |
| Maisine | − | Precirol | (+) |
| Capryol | − | GMS | − |
| Olive Oil | − | Dynasan 114 | − |
| Sesame Oil | − | Dynasan 116 | − |
| Soy bean oil | − | Gelucire 43/01 | − |
| Captex 200 | − | Gelucire 44/14 | − |
| Captex 355 | − | Gelucire 50/13 | − |
| Oleic acid | − | | |
| Castor Oil | + | | |

$^c$+: Soluble/dispersed, (+): Drug aggregated upon cooling, −: Drug remain aggregated Example 2 Preparation of AmB Loaded PEGylated NLCs (PEG-2K-NLC-AmB)

Amphotericin B loaded PEGylated NLCs were fabricated by hot-melt emulsification followed by high-pressure homogenization (HPH). The molecular weight of the PEG molecule attached to DSPE ranged from 1000 (1K) to 20,000 (20K). Thus, (mPEG 1,000-20,000-DSPE) was used for surface PEGylation.

Colloidal aqueous dispersion of Amphotericin B loaded NLC were prepared as per the formula in Table 2.

TABLE 2

Compositions of PEGylated and unPEGylated NLC.

| Ingredients | Amphotericin B loaded NLC Un-PEGylated NLC (% w/v) | PEG2K-NLC-AmB (% w/v) |
|---|---|---|
| Lipid Phase | | |
| Precirol ™ ATO 5 | 3 | 3 |
| Castor Oil | 1.5 | 2 |
| mPEG-DSPE. Na salt (1K, 2K, 5K, 10K, 20K) | 0 | 0.75 |
| Cremophor ® EL | 1.5 | 0 |
| Amphotericin B | 0.1 | 0.3 |
| Aqueous phase | | |
| Tween 80 | 0.8 | 0.8 |
| Poloxamer 188 | 0.3 | 0.3 |
| Glycerin | 2.5 | 2.5 |
| Water | QS | QS |

The lipid phase along with Amphotericin B was heated to 75° C. and a coarse emulsion was formed by dropwise addition of the aqueous phase to the lipid phase under magnetic stirring at 2000 rpm. Further, the ULTRA-TURRAX® T 25(IKA works INC., NC, USA) was used to homogenize the coarse emulsion into a fine emulsion at 16000 rpm (temperature: 60° C.). This fine emulsion was homogenized (temperature: 50° C.) at 1500 bars of pressure for 15 mins in high-pressure homogenization (HPH) (Emulsiflex C5-Avestin, Canada).

The PEG(2K)-NLC-AmB colloidal dispersion were prepared by substituting Cremophor® EL with mPEG-DSPE in the lipid phase.

The physical-chemical characteristics of the colloidal dispersion were evaluated after preparation and after 8 days storage at room temperature—FIGS. 1-4.

High-pressure liquid chromatography (HPLC) analysis: Amphotericin B was quantified using a previously published method with some modifications[32]. Amphotericin B was quantified using high-performance liquid chromatography, which includes a Waters 717 plus auto-sampler coupled with a Waters 2487 Dual λ Absorbance UV detector, a Waters 600 controller pump, and an Agilent 3395 Integrator. A Phenomenex Luna® PFP (2) column with 5 μ packing and dimensions 4.6 mm×250 mm was used for the analysis. The mobile phase was 0.05 N sodium acetate and acetonitrile mixed with the ratio of 7:3. The retention time for amphotericin B was 11.6 min, detected at the wavelength ($\lambda_{max}$) of 407 nm. The standard curve of amphotericin B, ranging from 0.1 μg/mL to 20 μg/mL, was prepared with a mixture containing equal proportions of dimethyl sulfoxide (DMSO) and methanol. The method was validated for precision (inter- and intra-day), accuracy, linearity, limit of quantification, and limit of detection.

Physicochemical characterization of the nanostructured lipid carrier

Assay, Drug Loading, and Entrapment Efficiency.

Amphotericin B was extracted from the NLCs with a 50:50 solvent mixture of DMSO and methanol. For the total drug content, the formulation (10 μL) was diluted 100 times with the solvent mixture (990 μL), stirred vigorously, and centrifuged at 13000 rpm. The drug in the supernatant was quantified using HPLC. Entrapment efficiency of the drug was calculated by determining the free unentrapped drug. The formulation was filtered through the Amicon® filters (pore size of 100,000 Daltons) at 5000 rpm. The drug in the filtrate was quantified with HPLC. Percent entrapped drug was calculated using equation 2.1, whereas, drug loading was calculated using equation 2.2.

$$\% \, EE = \frac{W_t - W_f}{W_t} \cdot 100 \quad (2.1)$$

$$\% \, DL = \frac{W_t - W_f}{W_1} \cdot 100 \quad (2.2)$$

where, $W_t$=Total amphotericin B content in the formulation
$W_f$=Amphotericin B in the aqueous phase
$W_1$=Total weight of the nanoparticles.

Particle Size, PDI, and Zeta Potential.

Dynamic light scattering (Zetasizer Nano ZS, Malvern Instruments, USA) was used to measure mean hydrodynamic particle size (z-average), PDI, and zeta potential. The formulations were diluted 100 times prior to measurements. All the measurements were made at 25° C.

Surprising results were observed; PEGylation (DSPE-PEG-2000-1.5% w/v) not only enhanced physical stability of the NLCs, but also enhanced amphotericin B loading and prevented its leaching over time (FIGS. 1, 2, 3, and 4). In addition to DSPE-PEG-2K, other DSPE-PEGs of varying molecular weight (1K, 5K, 10K, 20K) were tested for their ability to enhance drug loading. These preliminary investigations were carried out using probe sonication. The formulations using DSPE-PEG-10K and DSPE-PEG-20K were physically unstable and lipid aggregates were observed. NLC with DSPE-PEG-5K had black residues at the bottom of the vials, these indicated some type of chemical instability (either drug or lipid or DSPE-PEG-2K degradation). For ease of scale up and manufacturing, these formulations were then prepared using high pressure homogenizer.

Un-PEGylated NLC:

We observed that amphotericin B is chemically stable on autoclaving but the NLCs in the colloidal dispersion were physically unstable (statistically significant increase in particle size and PDI) at amphotericin B loads of 0.05% w/v and higher. This might be due to absence of bulky PEG corona surrounding NLC that protects and stabilizes them by steric hindrance. The drug precipitated out and formed a cake (not easily dispersed upon shaking) at the bottom.

DSPE-PEG-1K:

The formulations (colloidal dispersion) prepared with DSPE-PEG-1K was physically stable for 8 days, both pre- and post-autoclave. There was a decrease in amphotericin B content (statistically significant). Some precipitation was seen with the naked eyes (relatively more than 2K, but less than 5K) at the bottom of the vials but was redispersible. Note that a 7-14-day stability post reconstitution would be a significant advantage over what is currently available.

DSPE-PEG-2K:

Both pre- and post-autoclave formulations (colloidal dispersion) prepared with DSPE-PEG-2K were stable for 8 days. There was some precipitation seen at the bottom of the vials but was easily and completely redispersible. This precipitate might be larger lipid nanoparticles (PDI~0.3-0.35).

DSPE-PEG-5K:

There was statically significant increase in PDI post-autoclave, however the remaining formulation characteristics remained the same.

DSPE-PEG-10K and DSPE-PEG-20K:

There was significant drop in assay post-autoclave and the formulations were not physically stable. The post-autoclaved samples crystallized and froze at 4° C.

The formulations, 1K, 2K, 5K, were slightly orangish upon autoclaving. There was black residue seen in formulations which had DSPE-PEG (5K, 10K, and 20K). Over one-month there are large particles observed in formulations containing DSPE-PEG-10K and -20K.

TABLE 3

Visual inspection on day 1 and day 8 for amphotericin B loaded NLC (PEGylated and Un-PEGylated). mPEG-DSPE was used with varying PEG molecular weight—1K, 2K, 5K, 10K, 20K.

| Visual Inspection | Duration | Un-PEGylated NLC | PEGylated NLC | | | | |
|---|---|---|---|---|---|---|---|
| | | | DSPE-PEG-1K | DSPE-PEG-2K | DSPE-PEG-5K | DSPE-PEG-10K | DSPE-PEG-20K |
| Black Precipitation | Initial time | No ppt | No ppt. | No ppt. | No ppt. | Some ppt. | Moderate ppt. |
| | Day 81 | No ppt | No ppt | No ppt | some ppt. | Moderate ppt. | Extreme ppt. |
| | Month | No ppt | No ppt | No ppt | some ppt. | Extreme ppt. | Extreme ppt. |

TABLE 3-continued

Visual inspection on day 1 and day 8 for amphotericin B loaded NLC (PEGylated and Un-PEGylated). mPEG-DSPE was used with varying PEG molecular weight—1K, 2K, 5K, 10K, 20K.

| Visual Inspection | Duration | Un-PEGylated NLC | PEGylated NLC ||||| 
|---|---|---|---|---|---|---|---|
| | | | DSPE-PEG-1K | DSPE-PEG-2K | DSPE-PEG-5K | DSPE-PEG-10K | DSPE-PEG-20K |
| Re-dispersibility of settled nanoparticles/sedimented lipid | Day 81 | Easily redispersible (2-4 sec) | Easily redispersible (2-4 sec) | Easily redispersible (2-4 sec) | Redispersible (10-15 sec) | Redispersible (10-15 sec) | Redispersible (10-15 sec) |
| | Month 1 | Easily redispersible (2-4 sec) | Easily redispersible (2-4 sec) | Easily redispersible (2-4 sec) | No aggregation | Not easily redispersible | Not easily redispersible |
| Aggregation/Creaming | Month | No aggregation | No aggregation | No aggregation | No aggregation | Particle aggregation | Particle aggregation |

Example 3: In Vitro Antifungal Activity and Cytotoxicity Evaluation

Figure 5:
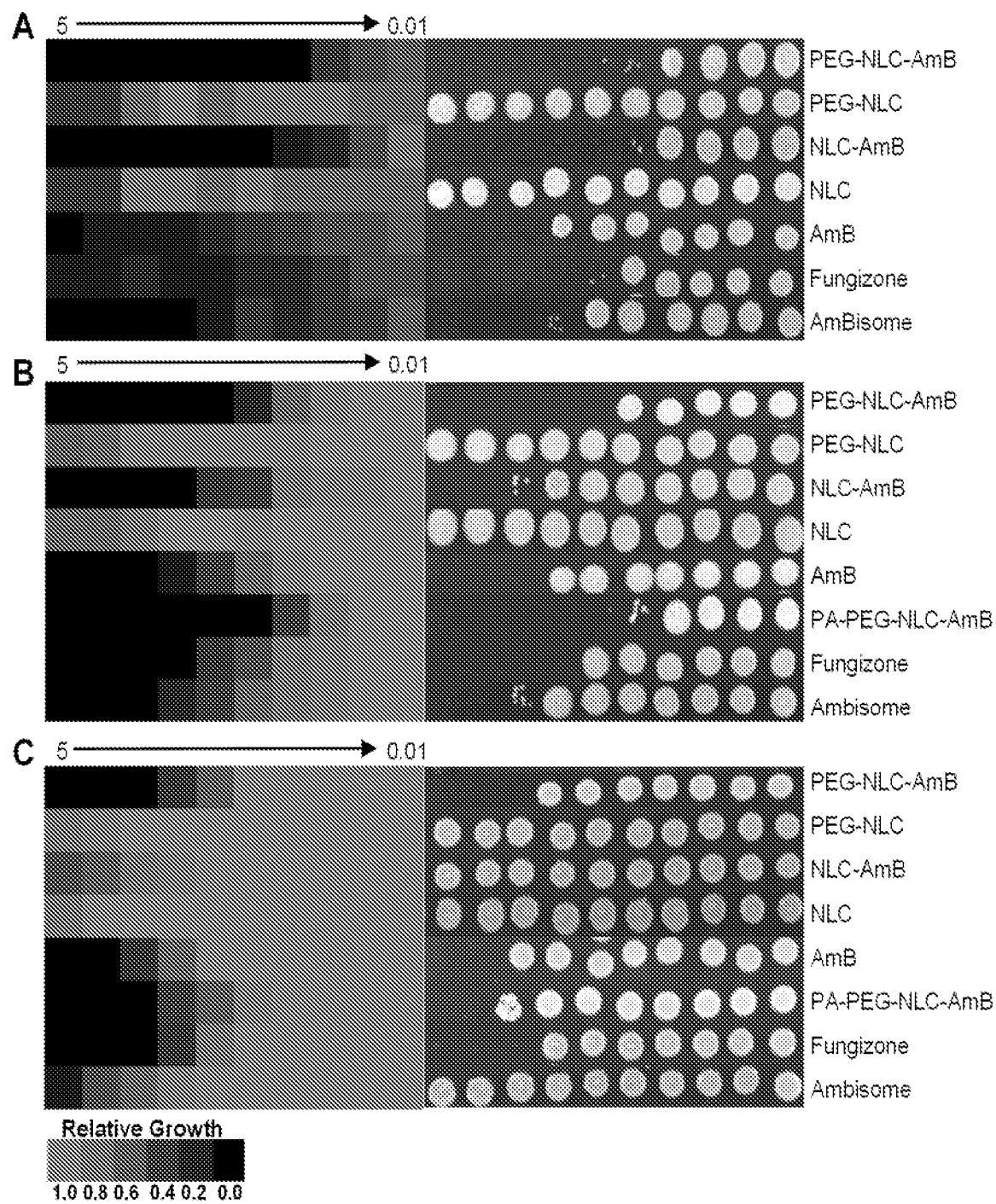
FIG. 5: Antifungal activity of amphotericin B formulations. Left panel shows Java Tree visualization of microdilution assay data. Right panel shows cell recovery on drug-free agar plates. Each formulation was tested at 5.0-0.01 µg/ml with 2-fold dilutions. Color bar represents relative growth. A. Antifungal activity on Day 1 post AmB formulation in wild type (WT) Candida. B. & C. Antifungal activity on Day 10 post AmB formulation in WT and AmB resistant Candida strains, respectively. Each experiment was performed in triplicates. Where, PEG-NLC-AmB is amphotericin B loaded PEGylated (PEG 2K) nanostructured lipid carriers; PA-PEG-NLC-AmB is autoclaved amphotericin B loaded PEGylated (PEG 2K) nanostructured lipid carriers; PEG-NLC is PEGylated (PEG 2K) blank nanostructured lipid carriers; NLC-AmB is amphotericin B unPEGylated nanostructured lipid carriers; NLC-blank unPEGylated nanostructured lipid carriers; Fungizone™ is marketed amphotericin B deoxycholate reconstituted in 5% dextrose; AmBisome® is marketed amphotericin B liposomes reconstituted using sterile water for injection.
Figure 6:
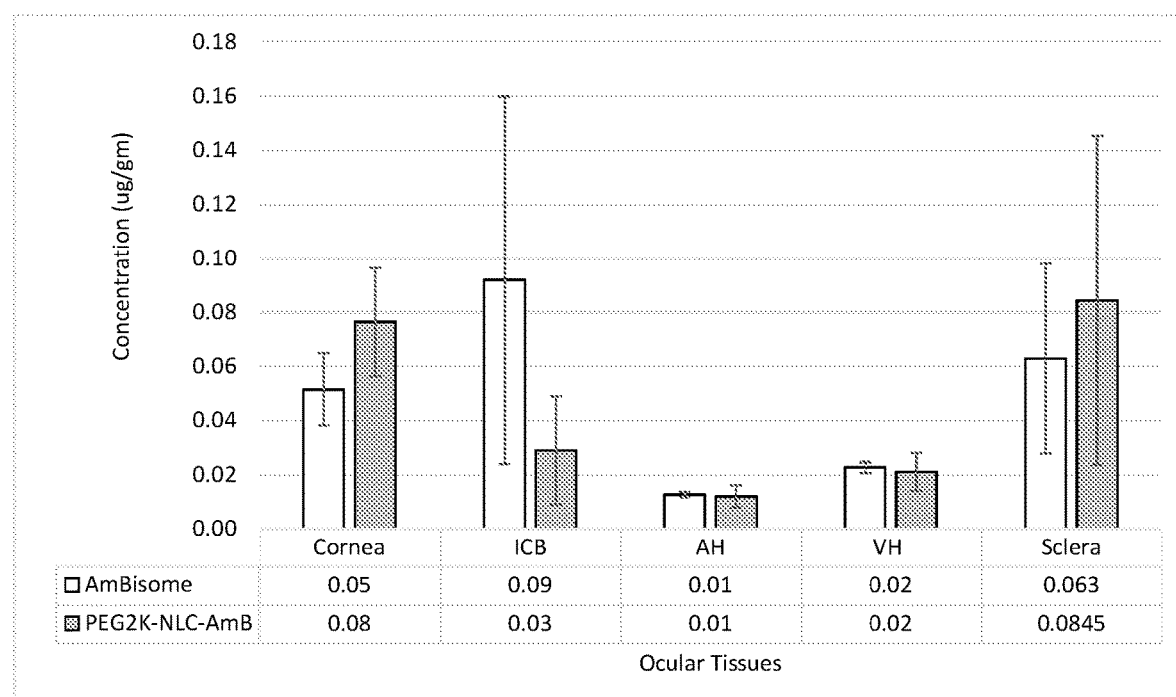
FIG. 6: Ocular biodistribution of amphotericin B loaded PEGylated (2K) NLC in comparison with AmBisome® (marketed preparation—freeze-dried liposome), in vivo in Albino New Zealand rabbits (Instillation volume 50 uL, Dose 150 ug every hour for 6 hours and sacrifice rabbits at $7^{th}$ hour). The difference in amphotericin B concentrations in the ocular tissues from the amphotericin B loaded PEGylated NLC were statistically insignificant (p>0.05) from the marketed preparation. The error bars represent standard error. Where, PEG2K-NLC-AmB is amphotericin B loaded PEGylated (2K) nanostructured lipid carriers.

In vitro fungicidal activity: A microdilution experiment was performed in wild type (WT) *Candida albicans* (ATCC90028) and *Aspergillus fumigatus* (ATCC 204305) as per Clinical & Laboratory Standards Institute (CLSI) protocols[37-39]. PEG2K-NLC-AmB, NLC-AmB, amphotericin B pure compound (AmB) and commercially available AmB formulations Fungizone® and AmBisome® were tested. Recovery assay was performed for fungicidal activity at both day 1 and day 10 post preparation. At day 1 in *Candida*, than the freshly prepared AmB, and 10 days old Fungizone® and AmBisome® formulations in both WT and AmB resistant *Candida* strain (FIG. 5 & Table 4). The fungicidal activity of the PEG2K-NLC-AmB was not affected on autoclaving the formulation. Based on the antifungal assays PEG2K-NLC-AmB, showed significantly better efficacy and stability in both WT and AmB resistant *Candida* strains and, is comparable to, or better than, commercially available AmB formulations like Fungizone® and AmBisome®. The placebo formulations (no AmB), PEG-NLC and NLC, did not exhibit any fungicidal activity.

TABLE 4

Summary of Antifungal profile of formulations. PEG2K used for PEGylation, ND—Not Done, NA—Not Achieved, PA—Post autoclave

| Formulations | *Candida albicans* (WT) (ATCC 90028) || AmB-resistant *Candida albicans* (ATCC 200955) || *Aspergillus fumigatus* (ATCC 204305) |
|---|---|---|---|---|---|
| | MIC (µg/mL) (Day1/Day10) | MFC (µg/mL) (Day1/Day10) | MIC (µg/mL) (Day10) | MFC (µg/mL) (Day10) | MIC (µg/mL) (Day1) |
| PEG-NLC-AmB | 0.08/0.31 | 0.16/0.31 | 1.25 | 1.25 | 1.25 |
| PEG-NLC | NA/NA | NA/NA | NA | NA | NA |
| NLC-AmB | 0.16/0.62 | 0.16/2.5 | NA | NA | 1.25 |
| NLC | NA/NA | NA/NA | NA | NA | NA |
| PA-PEG-NLC-AmB | ND/0.16 | ND/0.31 | 1.25 | 2.5 | ND |
| AmB | 0.62/0.62 | 1.25/1.25 | 2.5 | 2.5 | 2.5 |
| Fungizone | 0.31/0.62 | 0.31/0.63 | 1.25 | 1.25 | 0.62 |
| Ambisome | 0.62/1.25 | 0.62/2.5 | NA | NA | 1.25 |

PEG2K-NLC-AmB showed the strongest antifungal activity among AmB, Fungizone® and AmBisome® (FIG. 5 & Table 4). The recovery assay also established lowest minimum fungicidal concentration (MFC) value for PEG2K-NLC-AmB i.e. 0.16 µg/mL. Against *Aspergillus*, PEG2K-NLC-AmB showed lower MIC value (1.25 µg/ml) compared to AmB (2.5 µg/ml) and was comparable to AmBisome® (1.25 µg/ml). MIC with Fungizone® was 0.62 µg/ml (Table 5).

At day 10 post formulation, autoclaved PEG2K-NLC-AmB (PA-PEG2K-NLC-AmB) was also included in the matrix and fungicidal assay was performed in both WT and AmB resistant *Candida* strain (ATCC 200955) to determine the stability and efficacy of PEG2K-NLC-AmB formulation. At Day 10, PEG2K-NLC-AmB formulation is slightly less active than the day 1 post formulation but significantly better In vitro cytotoxicity evaluation: The placebo (no Amphotericin B) formulations PEG-NLC and NLC alone were tested for cytotoxicity towards the retinal pigmented epithelial cells (ATCC ARPE-19) in a concentration range of 0.03%-1%. PEG-NLC and NLC did not show any toxicity up to a highest concentration of 1%. The drug formulations PEG2K-NLC-AmB, NLC-AmB, AmB, PA-PEG2K-NLC-AmB, Fungizone® and AmBisome® were tested in the concentration range of 0.95-30 µg/mL. They were not cytotoxic to ARPE-19 cells up to a highest concentration of 30 µg/mL, indicating a high therapeutic index. The control drug benzalkonium chloride was toxic with an IC50 of 3.9 µg/mL. Moreover, histological evaluation of the rabbit corneas exposed to the formulations for 3 h (post corneal transport experiments) did not show any difference from that of the corneas exposed to the control formulations.

Example 4: Physical and Chemical Stability of the PEG(2K)-NLC-AmB Colloidal Dispersion Formulation Compared with Marketed Reconstituted Formulations

TABLE 5

Physicochemical evaluation for amphotericin B loaded unPEGylated NLC, amphotericin B loaded PEGylated NLC (pre-and post-autoclave) and amphotericin B loaded PEGylated NLC post reconstitution of freeze dried formulation.

| Stability | Day | PEG2K-NLC-AmB 0.05% | PEG2K-NLC-AmB 0.30% | PEG2K-NLC-AmB-Post reconstitution of freeze dried formulation (AFTER 4 MONTHS Storage) 0.30% | PEG2K-NLC-AmB Post autoclave 0.05% | PEG2K-NLC-AmB Post autoclave 0.30% | Un-PEGylated NLC 0.05% | Un-PEGylated NLC 0.30% |
|---|---|---|---|---|---|---|---|---|
| Physical Stability | Day 1/Day 30 | Very slight precipitation observed with 0.3% drug load only, easily redispersible. No precipitate in the 0.05% formulation. | | Very slight precipitation observed with 0.3% drug load only, easily redispersible. No precipitate in the 0.05% formulation | Very slight precipitation observed with 0.3% drug load only, easily redispersible. No precipitate in the 0.05% formulation | | Significant precipitation observed at both concentrations; not easily redispersible | |
| Particle Size (nm) | Day 1 | 302 ± 4.56 | 316 ± 8.77 | 315 ± 5.7 | 290.25 ± 5.7 | 285 ± 6.9 | 210 ± 1.44 | 208 ± 3.77 |
| | Day 30 (4 deg C.) | 308 ± 6.45 | 325 ± 15.47 | NA | NA | NA | NA | NA |
| PDI | Day 1 | 0.27 ± 0.01 | 0.35 ± 0.01 | 0.39 ± 0.05 | 0.25 ± 0.009 | 0.29 ± 0.006 | 0.25 ± 0.01 | 0.25 ± 0.01 |
| | Day 30 (4 deg C.) | 0.3 ± 0.06 | 0.36 ± 0.06 | NA | NA | NA | NA | NA |
| AmB content (%) | Day 1 | 95.16 ± 2.5 | 92.7 ± 2.5 | 92.7 ± 2.5 | 89.99 ± 3.5 | 92.26 ± 2.8 | 91.5 ± 0.8 | 116.9 ± 8.4 |
| | Day 30 (4 deg C.) | 93.6 ± 5 | 93.7 ± 7 | NA | NA | NA | NA | NA |
| Viscosity (cPs) | | 2.95 | 3.05 | NA | NA | NA | NA | NA |

NA—Not applicable or not studied.

Example 5: Compatibility with Benzalkonium Chloride (BAK)

A major drawback of the currently available amphotericin B formulations is that preservatives cannot be added to the formulations because of stability issues. The stability of various formulations prepared as per the invention against the marketed reconstituted solutions were tested. The formulations are presented in Table 6.

TABLE 6

Composition of PEG2K-NLC-AmB, Chitosan PEG2K-NLC-AmB, PEG2K-NLC-AmB gels.

| Components | Un-PEGylated NLC (% w/v) | PEG2K-NLC-AmB (% w/v) | Chitosan PEG2K-NLC-AmB (% w/v) | PEG2K-NLC-AmB Gels (% w/v) |
|---|---|---|---|---|
| Lipid Phase | | | | |
| Precirol™ ATO 5 | 3 | 3 | 3 | 3 |
| Castor Oil | 1.5 | 2 | 2 | 2 |
| mPEG(2K)-DSPE. Na salt | 0 | 0.75 | 0.75 | 0.75 |
| Cremophor ® EL | 1.5 | 0 | 0 | 0 |
| Amphotericin B | 1 | 3 | 3 | 3 |
| Aqueous phase | | | | |
| Tween 80 | 0.8 | 0.8 | 0.8 | 0.8 |
| Poloxamer 188 | 0.3 | 0.3 | 0.3 | 0.3 |
| Glycerin | 2.5 | 2.5 | 2.5 | 2.5 |
| Water | QS | QS | QS | QS |
| Xanthan gum | NA | NA | NA | 0.1 |
| Gellan gum | NA | NA | NA | 0.5 |
| Chitosan (Added once formulation is formed) | NA | NA | 0.1 | NA |

As seen in Table 7, addition of BAK to reconstituted AmBisome or Fungizone led to the formation of aggregates (7-8 fold increase in particle size and PDI 7 days after addition of BAK-0.05% w/v). On the other hand, addition of BAK to the PEG2K-NLC-AmB formulation did not lead to any change in the physical characteristics of the formulation (particle size or pDI). The BAK added formulations did not show any decrease in antifungal activity against *Candida* on Day 1; however, after 7 days a decrease in fungicidal activity was seen with the Ambisome+BAK and Fungizone+BAK formulations. Besides a decrease in antifungal activity, increase in particle size could also lead to variations in ocular absorption and can also cause irritation and thus induce lacrimation and drug loss. Addition of Chitosan or in situ gelling agents improved the physical stability of the formulations (Table 6 and 7).

by gently touching a pre-weighed piece of filter paper at the corneal surface at every time point (t=0, 0.25, 0.5, 1, 2, 4, and 6 hours). The wet weight of the filter paper was then recorded and the difference in their dry and wet weights was used in the determination of the amount of tear fluid that was collected, which was used in the estimation of amphotericin B from the tear biosamples.

TABLE 7

Effect on PS and PDI on addition of benzalkonium chloride to Amphotericin B formulations.

| | | | PEG2K-NLC-AmB | | PEG2K-NLC-AmB Chitosan | PEG2K-NLC-AmB Gel | AmBisome ® | | Fungizone ™ (D5W) | |
|---|---|---|---|---|---|---|---|---|---|---|
| | Stability | Day | 0.05% | 0.30% | 0.30% | 0.30% | 0.05% | 0.30% | 0.05% | 0.30% |
| | Physical Stability | Day 1/Day 30 | Very slight precipitation observed with 0.3% drug load only, easily redispersible. No precipitate in the 0.05% formulation | | Extremely small amount of precipitation observed for 2 months. Precipitation is significantly lower than 0.3% PEG-NLC-AmB. Precipitation was easily redispersible | No precipitation observed for 2 months | Clear solution | | Clear solution | |
| Before adding preservative | Particle Size(nm) | Day 1 | 302 ± 4.56 | 316 ± 8.77 | 375 ± 2.91 | 190 ± 6.2 | 100 ± 1.29 | 100 ± 1.29 | NA | NA |
| | | Day 30 (4 deg C.) | 308 ± 6.45 | 325 ± 15.47 | 389.6 ± 0.41 | 194 ± 2.4 | 105 ± 2.27 | 105 ± 2.27 | NA | NA |
| | PDI | Day 1 | 0.27 ± 0.01 | 0.35 ± 0.01 | 0.35 ± 0.009 | 0.25 ± 0.01 | 0.09 ± 0.02 | 0.12 ± .01 | NA | NA |
| | | Day 30 (4 deg C.) | 0.3 ± 0.06 | 0.36 ± 0.06 | 0.41 ± 0.006 | 0.27 ± 0.005 | 0.11 ± 0.06 | 0.07 ± 0.03 | NA | NA |
| | AmB content (%) | Day 1 | 95.16 ± 2.5 | 92.7 ± 2.5 | 105.15 ± 3.09 | 99.15 ± 1.2 | 112 ± 3.5 | 120 ± 4.5 | 126 ± 1.9 | 143 ± 0.1 |
| | | Day 30 (4 deg C.) | 93.6 ± 5 | 93.7 ± 7 | 102 ± 0.05 | 98.6 ± 0.19 | NA | 125 ± 6 | NA | 122.9 ± 0.6 |
| | Viscosity (cPs) | | 2.95 | 3.05 | 7.92 | 194.3 | NA | NA | NA | NA |
| Effect of Preservative (Benzalkonium Chloride) | Particle Size (nm) | Day 1 | 250 ± 10.5 | 220 ± 6.7 | 276 ± 2.5 | Formulation formed gel (Interaction with chitosan due to its positive charge) | NA | 96 ± 2.5 | NA | NA |
| | | Day 7 (4 deg C.) | 255 ± 2.4 | 212 ± 4.6 | 287 ± 5.6 | | NA | 708 ± 105 | NA | 1025 |
| | PDI | Day 1 | 0.29 ± 0.02 | 0.31 ± 0.03 | 0.39 ± 0.02 | | NA | 0.09 ± 0.02 | NA | NA |
| | | Day 7 (4 deg C.) | 0.30 ± 0.02 | 0.33 ± 0.02 | 0.4 ± 0.03 | | NA | 1 | NA | 1 |
| | AmB content (%) | Day 1 | 110.24 ± 2.7 | 106.67 ± 1.2 | NA | | NA | 113 ± 2.1 | NA | 115 ± 0.9 |
| | | Day 7 (4 deg C.) | 111.14 ± 1.3 | 105.8 ± 0.4 | NA | | NA | 112 ± 1.5 | NA | 116 ± 1.5 |
| | Viscosity (cPs) | | NA | NA | NA | NA | NA | NA | NA | NA |

NA = Not available or not studied.

Example 6: Ocular Precorneal Kinetics and Tissue Distribution Post Topical Application In vivo pre-corneal tear kinetics of the various amphotericin B formulations (PEG2K-NLC-AmB, Chitosan PEG2K-NLC-AmB, PEG2K-NLC-AmB Gel, AmBisome®, Fungizone) was determined in male New Zealand White Albino Rabbits, weighing 2-2.5 kg, which were procured from Charles River Labs. All the animal studies conformed to the tenets of the Association for Research in Vision and Ophthalmology statement on the use of animals in ophthalmic vision and research and the University of Mississippi Institutional Animal Care and Use Committee approved protocols. The rabbits were dosed (50 μL) with amphotericin B formulations topically. Therefore, the amount of amphotericin B dose received by the rabbits would be 0.15 mg from all the formulations tested. The tear samples were collected The extraction of amphotericin B from the tear biosamples collected on filter papers was performed by adding six hundred microliters of 50:50 mixture of ice-cold methanol and dimethyl sulfoxide, mixing thoroughly using a vortex genie mixer, and then centrifuging at 13,000 rpm for 15 minutes in a table-top centrifuge. The supernatant was then collected and analyzed for amphotericin B using a validated HPLC quantification method that has been outlined above (0073). The data was then analyzed using PKNCA package using R to determine various PK parameters [12]. Once the study was completed, Balanced Salt Solution (BSS) was used for washing the test eyes of the rabbits during the wash-out period.

Bioanalytical Method for quantification of amphotericin B in ocular tissues: For quantification of amphotericin B in the in vivo samples, a Waters Xevo TQ-S triple quadrupole tandem mass spectrometer with an electrospray ionization source, equipped with the ACQUITY UPLC® I-Class System was used (Waters Corporation, Milford, Mass., USA). Data acquisition was performed with Waters Xevo TQ-S quantitative analysis TargetLynx software and data processing was executed with MassLynx mass spectrometry software. Separation operations were accomplished using a C18 column (Acquity UPLC® BEH C18 100 mm×2.1 m, 1.7 μm particle size). The mobile phase consisted of water (A), and acetonitrile (B) both containing 0.1% formic acid at a flow rate of 1.0 mL/min with a gradient elution as follows: 0 min, 98% A/2% B held for 0.2 minutes and in next 2.3 min to Ocular biodistribution of Amphotericin from the PEGylated (2K) NLC was found to be similar to the marketed preparation (AmBisome®-Liposomal Amphotericin B preparation).

In vivo, ocular biodistribution of amphotericin B was studied in 8 male New Zealand albino rabbits (weighing around 2-2.5 kg), procured from Harlan Labs (Indianapolis, Ind., USA). All animal studies conformed to the tenets of the Association for Research in Vision and Ophthalmology statement on the use of animals in ophthalmic vision and research and the

TABLE 8

Parameters obtained from non-compartmental analysis of in vivo precorneal kinetics data.

| Parameter | Unit | Fungizone ™ | AmBisome ® | PEG2K-NLC-AmB | Chitosan PEG2K-NLC-AmB | PEG2K-NLC-AmB Gel |
|---|---|---|---|---|---|---|
| $t_{1/2}$ | h | 1.54 | 4.77 | 2.26 | 4.51 | 17.66 |
| Cmax/C0 | μg/μl | 4.74 | 5.36 | 4.90 | 5.68 | 7.84 |
| Clast_obs/Cmax | | 0.00 | 0.00 | 0.00 | 0.01 | 0.00 |
| AUC 0-t | μg/μl*h | 0.85 | 0.76 | 1.19 | 1.27 | 2.05 |
| AUC 0-inf_obs | μg/μl*h | 0.88 | 0.81 | 1.24 | 1.46 | 2.75 |
| AUMC 0-inf_obs | μg/μl*h^2 | 0.38 | 0.84 | 0.94 | 3.16 | 22.96 |
| MRT 0-inf_obs | h | 0.43 | 1.04 | 0.76 | 2.17 | 8.35 |

University of Mississippi Institutional Animal Care and Use Committee approved protocols.

100% B. Each run was followed by a 1-minute wash with 100% B and an equilibration period of 2 minutes with 98% A/2% B. The column and sample temperature were maintained at 50° C. and 10° C., respectively. The effluent from the LC column was directed into the ESI probe. Mass spectrometer conditions were optimized to obtain maximal sensitivity. The following conditions were used for the electrospray ionization (ESI) source: source temperature 150° C., desolvation temperature 600° C., capillary voltage 3.0 kV, cone voltage 40 V, nebulizer pressure, 7 bar and nebulizer gas 1100 L·h$^{-1}$N$_2$. Argon was used as the collision gas. The collision energies were optimized and ranged from 10 to 15 eV for individual analytes. Instrument control and data processing were performed by using MassLynx software (version 4.1, Waters, Milford, Mass., USA). Mass spectra were acquired in positive mode and multiple reaction monitoring (MRM) mode. The multiple reaction monitoring (MRM) mode was applied to monitor the transitions of quantifier ion to qualifier ions (the precursor to fragment ions transitions) of m/z 924.4→m/z 107.5, 743.2, 761.4 for amphotericin B and m/z 666.2→m/z 467.2, 485.2, 503.2 for natamycin. Natamycin was used as the internal standard. Confirmation of compounds was achieved through three fragment ions.

Amphotericin B was quantified—by inverse prediction of concentration from the peak area obtained for LC-MS/MS—using a calibration curve (coefficient of determination r$^2$≥0.98) determined for ocular tissues, such as the cornea, Iris-Ciliary Bodies, Aqueous Humor, Vitreous Humor, and Sclera. The process and extraction efficiency were greater than 90% for all the tissues.

The concentration time-profile of amphotericin B in the tear demonstrated that the gel formulation was retained on the ocular surface for a much longer duration (Table 8). This could lead to decreased dosing frequency.

Figure 7:
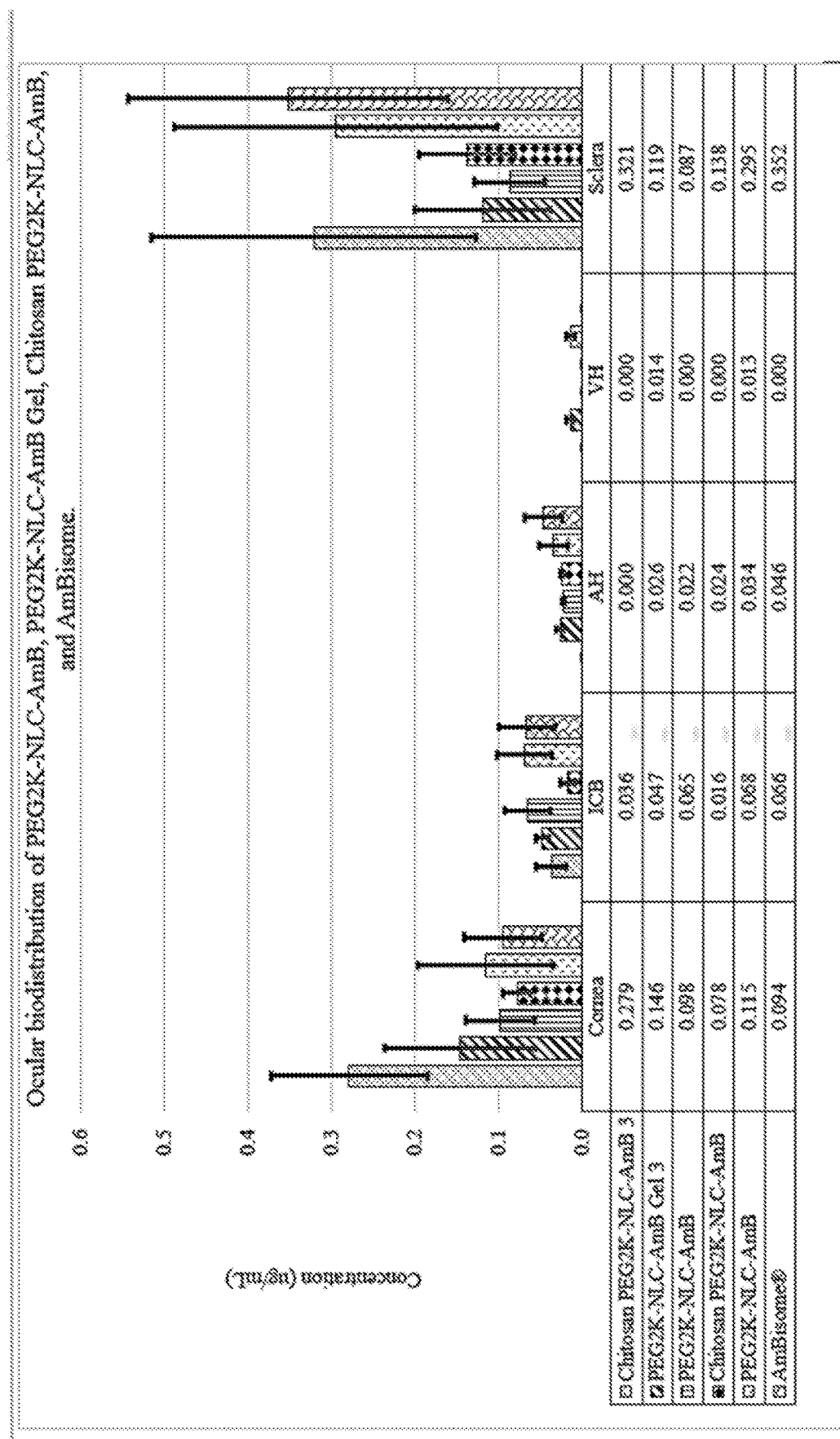
FIG. 7: Ocular biodistribution of amphotericin B from amphotericin B loaded PEGylated (2K) NLC, chitosan coated PEGylated (2K) NLC, and PEGylated (2K) NLC entrapped in ion sensitive gels in comparison with AmBisome® (marketed preparation—freeze-dried liposome), in vivo in Albino New Zealand rabbits (Instillation volume 50 uL, Dose 150 ug). The concentration of amphotericin B for amphotericin B loaded PEGylated NLC, chitosan coated PEGylated (2K) NLC, and PEGylated (2K) NLC entrapped in ion sensitive gels in ocular tissues were statistically insignificant (p>0.05) in comparison to concentrations of amphotericin B from marketed preparation. The error bars represent standard error. Where, PEG2K-NLC-AmB is amphotericin B loaded PEGylated nanostructured lipid carriers; Chitosan PEG2K-NLC-AmB is chitosan coated PEGylated nanostructured lipid carriers; PEG2K-NLC-AmB Gel is PEGylated amphotericin B loaded nanostructured lipid carriers entrapped in in situ gelling systems; AmBisome® is marketed amphotericin B liposomes reconstituted using sterile water for injection. Dosing regimen for PEG2K-NLC-AmB, chitosan PEG2K-NLC-AmB, and PEG2K-NLC-AmB Gel is 150 ug every 2 hours for 6 hours and sacrifice rabbits at $8^{th}$ hour. Whereas, dosing regimen for chitosan PEG2K-NLC-AmB 3, and PEG2K-NLC-AmB Gel 3 is 150 ug every 3 hours for 6 hours and sacrifice rabbits at $9^{th}$ hour.

The amphotericin B formulations, were evaluated in vivo in conscious rabbits (n=4). Six doses of each formulation (Table 6) were administered (50 μL each) 60 min apart. One-hour post-instillation of the final dose, the rabbits were euthanized, under anesthesia, with an overdose of pentobarbital injected through a marginal ear vein. The eyes were washed thoroughly with ice-cold phosphate-buffered saline and enucleated. All the ocular tissues were separated and homogenized; The drug was extracted from the tissues using an ice-cold solvent mixture (9:1-methanol: DMSO) and analyzed for amphotericin B content according to the procedure described in Section Bioanalytical method development. Data from the studies are presented in FIG. 7. The ocular concentrations generated from the PEGylated amphotericin B formulations were not statistically different from the marketed formulation. The gel formulation achieved similar ocular tissue concentrations with a reduced dosing frequency (every 3 h vs every 2 h).

The present application can "comprise" (open ended) or "consist essentially of" the components of the present invention as well as other ingredients or elements described herein. As used herein, "comprising" is open ended and means the elements recited, or their equivalent in structure or function, plus any other element or elements which are not recited. The terms "having" and "including" are also to be construed as open ended unless the context suggests otherwise.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, "optional" or "optionally" means that the subsequently described event or circumstance does or does not occur and that the description includes instances where said event or circumstance occurs and instances where it does not. For example, an optionally variant portion means that the portion is variant or non-variant.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, the term "subject" refers to a target of administration. The subject of the herein disclosed methods can be a mammal. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. A "patient" refers to a subject afflicted with a disease or disorder. The term "patient" includes human and veterinary subjects.

As used herein, the term "effective amount" refers to an amount that is sufficient to achieve the desired result or to have an effect on an undesired condition. For example, the term "therapeutically effective amount" refers to an amount that is sufficient to achieve the desired therapeutic result or to have an effect on undesired symptoms, but is generally insufficient to cause adverse side effects. The specific therapeutically effective dose level for any particular subject will depend upon a variety of factors including the disorder being treated and the severity of the disorder; the specific composition employed; the age, body weight, general health, sex and diet of the subject; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, when a pharmaceutical is disclosed, as is understood in the art, all common forms and preparations of the pharmaceutical are also disclosed. For example, when the pharmaceutical amphotericin B is disclosed, a person having ordinary skill in the art will readily recognize forms such as amphotericin B trihydrate and solubilized amphotericin B, are also disclosed. In addition when the pharmaceutical amphotericin B is disclosed, a person having ordinary skill in the art will readily recognize preparations of amphotericin B of different purities are also disclosed including as a non-limiting example 80%, greater than 95%, and high purity amphotericin B. High purity amphotericin B generally refers to commercially purchased amphotericin B further purified by methods common in the art including high pressure liquid chromatography.

All publications, patents, and patent applications mentioned in this specification are herein incorporated by reference to the same extent as if each individual publication, patent, or patent application was specifically and individually indicated to be incorporated by reference, including the references set forth in the following list:

REFERENCES

1. Klotz S A, Penn C C, Negvesky G J, Butrus S I. Fungal and parasitic infections of the eye. Clin Microbiol Rev. 2000; 13(4):662-685.
2. Ellis D. Amphotericin B: spectrum and resistance. J Antimicrob Chemother. 2002; 49 Suppl 1(suppl 1):7-10.
3. Gallis H A, Drew R H, Pickard W W. Amphotericin B: 30 years of clinical experience. Rev Infect Dis. 1990; 12(2): 308-329.
4. Ghannoum M, Rice L. Antifungal Agents: Mode of Action, Mechanisms of Resistance, and Correlation of These Mechanisms with Bacterial Resistance. Clin Microbiol Rev. 1999; 12(4):501-517.
5. Green W, Bennett J, Goos R. Ocular penetration of amphotericin b: A report of laboratory studies and a case report of postsurgical cephalosporium endophthalmitis. Arch Ophthalmol. 1965; 73(6):769-775.
6. Cholkar K, Gilger B C, Mitra A K. Topical delivery of aqueous micellar resolvin E1 analog (RX-10045). Int J Pharm. 2016; 498(1-2):326-334.
7. Cholkar K, Patel S P, Vadlapudi A D, Mitra A K. Novel strategies for anterior segment ocular drug delivery. J Ocul Pharmacol Ther. 2013; 29(2):106-123.

8. Patel A, Cholkar K, Agrahari V, Mitra A. Ocular drug delivery systems: An overview. World J Pharmacol. 2013; 2(2):47-64.
9. Cholkar K, Patel S, Vadlapudi A, Mitra A. Novel Strategies for Anterior Segment Ocular Drug Delivery. J Ocul Pharmacol Ther. 2013; 29(2):106-123.
10. Cholkar K, Patel A, Vadlapudi A D, Mitra A K. Novel Nanomicellar Formulation Approaches for Anterior and Posterior Segment Ocular Drug Delivery. Recent Pat Nanomed. 2012; 2(2):82-95.
11. Cholkar K, Patel A, Vadlapudi A, Mitra A. Novel Nanomicellar Formulation Approaches for Anterior and Posterior Segment Ocular Drug Delivery. Recent patents on nanomedicine. 2012; 2(2):82-95.
12. Gaudana R, Ananthula H K, Parenky A, Mitra A K. Ocular Drug Delivery. AAPS J. Vol 122010:348-360.
13. Chhonker Y S, Prasad Y D, Chandasana H, et al. Amphotericin-B entrapped lecithin/chitosan nanoparticles for prolonged ocular application. Int J Biol Macromol. 2015; 72:1451-1458.
14. Walteçá Louis Lima da Silveira BPGLDLFFILSRKS-SALSMJMGA, Egito ESTd. Development and Characterization of a Microemulsion System Containing Amphotericin B with Potential Ocular Applications. 2017.
15. Jansook P, Pichayakorn W, Muankaew C, Loftsson T. Cyclodextrin-poloxamer aggregates as nanocarriers in eye drop formulations: dexamethasone and amphotericin B. Drug Dev Ind Pharm. 2016; 42(9):1446-1454.
16. Veronese F M, Pasut G. PEGylation, successful approach to drug delivery. Drug Discov Today. 2005; 10(21):1451-1458.
17. Balguri S, Adelli G, Bhagav P, Repka M, Majumdar S. Development of nano structured lipid carriers of ciprofloxacin for ocular delivery: Characterization, in vivo distribution and effect of PEGylation. Invest Ophthalmol Vis Sci. 2015; 56(7):2269-2269.
18. Muddineti O S, Kumari P, Ajjarapu S, et al. Xanthan gum stabilized PEGylated gold nanoparticles for improved delivery of curcumin in cancer. Nanotechnology. 2016; 27(32):325101.
19. Sanders N N, Peeters L, Lentacker I, Demeester J, De Smedt S C. Wanted and unwanted properties of surface PEGylated nucleic acid nanoparticles in ocular gene transfer. J Control Release. 2007; 122(3):226-235.
20. VANDANA BHARAT PATRAVALE PAP, Inventor; VANDANA BHARAT PATRAVALE, assignee. LIPIDIC NANOPARTICLES BASED COMPOSITION AND METHOD OF FORMULATION AND USE thereof. U.S. Pat. No. 279,598. Jan. 27, 2017, 2017.
21. Chaudhari M B, Desai P P, Patel P A, Patravale V B. Solid lipid nanoparticles of amphotericin B (AmbiOnp): in vitro and in vivo assessment towards safe and effective oral treatment module. Drug Deliv Transl Res. 2016; 6(4):354-364.
22. Patel P A, Patravale V B. AmbiOnp: solid lipid nanoparticles of amphotericin B for oral administration. J Biomed Nanotechnol. 2011; 7(5):632-639.
23. Butani D, Yewale C, Misra A. Topical Amphotericin B solid lipid nanoparticles: Design and development. Colloids Surf B Biointerfaces. 2016; 139:17-24.
24. Amekyeh H, Billa N, Yuen K H, Chin S L. A gastrointestinal transit study on amphotericin B-loaded solid lipid nanoparticles in rats. AAPS PharmSciTech. 2015; 16(4): 871-877.
25. Garse H, Jagtap P, Kadam V. Solid lipid nanoparticles based gel for topical delivery of antifungal agent. International Journal of Pharmaceutical Sciences and Research. 2015; 6(8):3571.
26. Tripathi P, Verma A, Dwivedi P, et al. Formulation and characterization of amphotericin b loaded nanostructured lipid carriers using microfluidizer. Journal of Biomaterials and Tissue Engineering. 2014; 4(3):194-197.
27. Fu T, Yi J, Lv S, Zhang B. Ocular amphotericin B delivery by chitosan-modified nanostructured lipid carriers for fungal keratitis-targeted therapy. J Liposome Res. 2017; 27(3):228-233.
28. Jung S H, Lim D H, Jung S H, et al. Amphotericin B-entrapping lipid nanoparticles and their in vitro and in vivo characteristics. Eur J Pharm Sci. 2009; 37(3-4):313-320.
29. Nimtrakul P, Tiyaboonchai W, Lamlertthon S. Effect of types of solid lipids on the physicochemical properties and self-aggregation of amphotericin B loaded nanostructured lipid carriers (NLCs). Asian Journal of Pharmaceutical Sciences. 2016; 11(1):172-173.
30. Tan S W, Billa N, Roberts C R, Burley J C. Surfactant effects on the physical characteristics of Amphotericin B-containing nanostructured lipid carriers. Colloids and Surfaces A: Physicochemical and Engineering Aspects. 2010; 372(1-3):73-79.
31. Tan S, Billa N, Roberts C. Mucoadhesive Chitosan-Coated Nanostructured Lipid Carriers for Oral Delivery of Amphotericin B. World Academy of Science, Engineering and Technology, International Journal of Chemical and Molecular Engineering. 2018; 5(3).
32. Betto P, Rajevic M, Boss E, Gradoni L. Improved Assay for Serum Amphotericin-B by Fast High Performance Liquid Chromatography. Journal of Liquid Chromatography & Related Technologies. 1997; 20(12):1857-1866.
33. Zhang L, Chan J M, Gu F X, et al. Self-assembled lipid—polymer hybrid nanoparticles: a robust drug delivery platform. ACS Nano. 2008; 2(8):1696-1702.
34. Vadlapudi A D, Vadlapatla R K, Earla R, et al. Novel biotinylated lipid prodrugs of acyclovir for the treatment of herpetic keratitis (HK): transporter recognition, tissue stability and antiviral activity. Pharm Res. 2013; 30(8): 2063-2076.
35. Majumdar S, Hingorani T, Srirangam R, Gadepalli R S, Rimoldi J M, Repka M A. Transcorneal permeation of L- and D-aspartate ester prodrugs of acyclovir: delineation of passive diffusion versus transporter involvement. Pharm Res. 2009; 26(5):1261-1269.
36. Tak R V, Pal D, Gao H, Dey S, Mitra A K. Transport of acyclovir ester prodrugs through rabbit cornea and SIRC-rabbit corneal epithelial cell line. J Pharm Sci. 2001; 90(10):1505-1515.
37. CLSI. Reference Method for Broth Dilution Antifungal Susceptibility Testing of Filamentous Fungi. Approved Standard-Second Edition ed. Wayne, Pa. 2008.
38. CLSI. Reference Method for Broth Dilution Antifungal Susceptibility Testing of Filamentous Fungi. CLSI document M38-A2. Approved Standard-Second Edition ed. Wayne, Pa. 2008.
39. CLSI. Reference method for broth dilution antifungal susceptibility testing of yeasts; approved standard. approved standard—third edition ed. Wayne, Pa. 2008.

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A nanostructured lipid carrier (NLC) comprising:
a combination of solid and liquid lipids; and
a polyethylene glycol (PEG) molecule, wherein the PEG has a molecular weight of between about 1000 and 5000, and
wherein the PEG molecule is partially or completely on the surface of the NLC.

2. The NLC of claim 1, wherein the PEG molecule has a molecular weight of between about 1000 and 3000.

3. The NLC of claim 1, wherein the PEG molecule has a molecular weight of about 2000.

4. The NLC of claim 1, wherein the PEG molecule is added as a PEG-lipid conjugate.

5. The NLC of claim 4, wherein the PEG-lipid conjugate is polyethylene glycol-2000-1,2-distearoyl-sn-glycero-3-phosphatidylethanolamine (PEG-2000-DSPE).

6. The NLC of claim 1, wherein the liquid lipid is castor oil.

7. The NLC of claim 1, further comprising a pharmaceutical, or combination of pharmaceuticals.

8. The NLC of claim 7, wherein the pharmaceutical is amphotericin B.

9. The NLC of claim 8, wherein the concentration of amphotericin B in a colloidal aqueous dispersion is from about 0.01% to about 0.5% w/v.

10. The NLC of claim 7, further comprising a cryoprotectant.

11. The NLC of claim 8, wherein the amphotericin B is loaded at about 1% to about 10% w/w of lipid content.

12. The NLC of claim 8, wherein the amphotericin B is loaded at about 4% to about 6% w/w of lipid content.

13. The NLC of claim 1, wherein the NLC has an average particle size of between about 200 nm and about 750 nm.

14. The NLC of claim 7, further comprising a preservative.

15. The NLC of claim 7, further comprising polymeric ingredients to further stabilize and/or impart mucoadhesive characteristics to the NLC.

16. The NLC of claim 15, wherein the polymeric ingredients comprise chitosan.

17. The NLC of claim 1, wherein the solid lipid is glyceryl distearate or glyceryl palmitostearate.

18. The NLC of claim 1, wherein the NLC is provided as a powder or cake or in a colloidal aqueous dispersion.

19. The NLC of claim 18, wherein the NLC is provided in an in situ gelling colloidal dispersion.

20. The NLC of claim 14, wherein the preservative is Benzalkonium Chloride.

* * * * *